United States Patent
He et al.

(10) Patent No.: US 11,318,151 B2
(45) Date of Patent: May 3, 2022

(54) COMPOUND PHARMACEUTICAL COMPOSITION FOR TREATING SKIN INFLAMMATORY DISEASES

(71) Applicants: Hefei Industrial Pharmaceutical Institute Co., Ltd., Anhui (CN); Hefei Amvite Pharmaceutical Co., Ltd, Anhui (CN)

(72) Inventors: Guangwei He, Anhui (CN); Zhaoxing Chu, Anhui (CN); Qinlong Xu, Anhui (CN); Jiajia Mo, Anhui (CN); Yan Zhao, Anhui (CN); Lincui Bian, Anhui (CN); Yuanfeng Gu, Anhui (CN); Li Shao, Anhui (CN)

(73) Assignees: HEFEI INDUSTRIAL PHARMACEUTICAL INSTITUTE CO., LTD, Anhui (CN); HEFEI AMVITE PHARMACEUTICAL CO., LTD, Anhui (CN)

( * ) Notice: Subject to any disclaimer, the term of this patent is extended or adjusted under 35 U.S.C. 154(b) by 90 days.

(21) Appl. No.: 16/761,996

(22) PCT Filed: May 9, 2019

(86) PCT No.: PCT/CN2019/086094
§ 371 (c)(1),
(2) Date: May 6, 2020

(87) PCT Pub. No.: WO2019/242422
PCT Pub. Date: Dec. 26, 2019

(65) Prior Publication Data
US 2020/0352965 A1    Nov. 12, 2020

(30) Foreign Application Priority Data
Jun. 20, 2018 (CN) .......................... 201810637196.3

(51) Int. Cl.
*A61K 31/69* (2006.01)
*A61P 17/00* (2006.01)
*A61K 9/00* (2006.01)
*A61K 31/519* (2006.01)

(52) U.S. Cl.
CPC ............ *A61K 31/69* (2013.01); *A61K 9/0014* (2013.01); *A61K 31/519* (2013.01); *A61P 17/00* (2018.01)

(58) Field of Classification Search
CPC .... A61K 31/69; A61K 9/0014; A61K 31/519; A61K 47/10; A61K 9/06; A61P 17/00; A61P 17/08; A61P 29/00; A61P 17/06; A61P 43/00
USPC .......................................................... 514/64
See application file for complete search history.

(56) References Cited

U.S. PATENT DOCUMENTS

2017/0152273 A1* 6/2017 Merchant ................. A61K 9/06

FOREIGN PATENT DOCUMENTS

| CN | 108992454 | 12/2018 |
|---|---|---|
| WO | 2017093857 | 6/2017 |

OTHER PUBLICATIONS

Written Opinion and International Search Report of PCT/CN2019/086094 dated Aug. 9, 2019, 12 pages (English and Chinese).

* cited by examiner

*Primary Examiner* — Taylor V Oh
(74) *Attorney, Agent, or Firm* — Rankin, Hill & Clark LLP

(57) ABSTRACT

The disclosure relates to the field of pharmaceutical technology, in particular, to a compound pharmaceutical composition for treating skin inflammatory diseases, which is characterized in that an active ingredient of the compound pharmaceutical of the disclosure is composed of tofacitinib and crisaborole, and the composition has a stronger therapeutic effect and a lower dosage with a significant synergistic therapeutic effect. The pharmaceutical composition of the disclosure can be used to treat skin inflammatory diseases.

11 Claims, No Drawings

COMPOUND PHARMACEUTICAL COMPOSITION FOR TREATING SKIN INFLAMMATORY DISEASES

TECHNICAL FIELD

The disclosure relates to the field of pharmaceutical technology, in particular, to a compound pharmaceutical composition for treating skin inflammatory diseases. The pharmaceutical composition of the disclosure can be used to treat skin inflammatory diseases.

BACKGROUND

Inflammation is a common and important basic pathological process. Body trauma infections and most common and multiple diseases of various organs are inflammatory diseases. [Cruz-Migoni S, Caamaño J. Fat-Associated Lymphoid Clusters in Inflammation and Immunity [J]. Front Immunol. 2016, 7: 612]. Skin inflammatory diseases include a variety of diseases characterized by skin inflammation and itching, such as atopic dermatitis, eczema, psoriasis, contact dermatitis, allergic dermatitis, seborrheic dermatitis, contact dermatitis, systemic lupus erythematosus, etc.

Inflammation and itching of the skin are two important characteristics of skin inflammatory diseases. JAK-STAT signaling pathway is a signal transduction pathway stimulated by cytokines, involved in many important biological processes such as cell proliferation, differentiation, apoptosis, and immune regulation. The JAK-STAT pathway is closely related to the occurrence and development of various inflammations. Recent studies have found that the JAK-STAT pathway is also closely related to skin itching, and many cytokines and growth factors conduct signals through the JAK-STAT signaling pathway, including TSLPIL-2-IL7), GM-CSF (granulocyte/macrophage colony-stimulating factor), GH (growth hormone), EGF (epidermal growth factor), PDGF (platelet-derived factor), and IFN (interferon) and so on. And, TSLP is considered to be the main cause of skin itching. Tofacitinib is a JAK1/JAK3 inhibitor developed by Pfizer for the treatment of rheumatoid arthritis. Recent clinical phase II studies have found that topical 2% tofacitinib has a certain therapeutic effect on atopic dermatitis and can improve itching symptoms in patients.

Phosphodiesterases (PDEs) are a super-family capable of catalyzing the hydrolysis of cAMP and/or cGMP. [Murthy V S, Mangot A G. Psychiatric aspects of phosphodiesterases: An overview [J]. Indian J Pharmacol, 2015, 47(6): 594-599]. Cyclic adenosine monophosphate (cAMP) can inhibit multiple functions of inflammation and inflammatory cells, and plays an important role in many diseases and conditions. In these cells, cAMP-specific PDE4 is the main form of PDE, and the PDE4 inhibitor can increase cAMP levels, so as to be used for, but not limited to, inflammation, asthma, and other conditions. [Parikh N, Chakraborti A K. Phosphodiesterase4 (PDE4) Inhibitors in the Treatment of COPD: Promising Drug Candidates and Future Directions [J]. Curr Med Chem, 2016, 23(2): 129-41]. Crisaborole is a topical PDE-4 inhibitor approved in 2016 for the treatment of atopic dermatitis.

The structural formulas for tofacitinib and crisaborole are as follows:

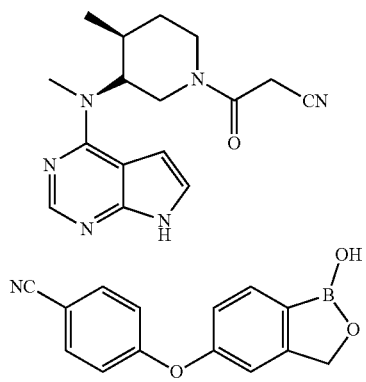

However, at present, the above drugs have certain defects in clinical use, so it is still important to find or develop new therapeutic drugs with better efficacy.

SUMMARY

By combining tofacitinib and crisaborole in a fixed dose ratio, the disclosure unexpectedly finds that the composition has a stronger therapeutic effect and a lower dosage with a significant synergistic therapeutic effect, while having strong clinical use value.

The disclosure discloses a compound pharmaceutical composition of tofacitinib and crisaborole. Pharmacodynamic test proves that the compound pharmaceutical composition of the disclosure has significant synergistic therapeutic effect in treating skin diseases caused by itching and inflammation, with a stronger therapeutic effect and a lower dosage.

Among them, preferably, a weight ratio of tofacitinib and crisaborole has a range of 1:8 to 8:1. Preferably, the compound pharmaceutical composition of the disclosure is a dosage form for topical administration, which is preferably cream, ointment, gel, foam, powder, tincture, lotion, spray or patch. The composition of the disclosure is used for the treatment of skin inflammatory diseases, including, but not limited to allergic dermatitis, urticaria, atopic dermatitis, seborrheic dermatitis, or contact dermatitis, and inflammatory skin reactions caused by immune diseases such as psoriasis and systemic lupus erythematosus.

The following are some of the pharmacodynamic tests and results of the compound pharmaceutical composition of the disclosure:

1. Therapeutic Effects of the Compound Pharmaceutical Composition of the Disclosure on a Phorbol Ester-Induced Mouse Ear Swelling Model SPF ICR mice, male, 18-22 g, randomly divided into compound groups with different compound ratios and a model group according to body weight, 10 mice for each group. The test drug is dissolved in a 20 μL solvent of DMSO. The specific group numbers are as follows:

(1) Compound groups with different compound ratios
Tofacitinib:crisaborole=2 mg:2 mg/20 μL (dose ratio=1:1; group a); tofacitinib:crisaborole=2 mg:1 mg/20 μL (dose ratio=2:1; group b); tofacitinib:crisaborole=2 mg:0.5 mg/20 μL (dose ratio=4:1; group c); tofacitinib:crisaborole=2 mg:0.25 mg/20 μL (dose ratio=8:1; group d); tofacitinib:crisaborole=2 mg:0.2 mg/20 μL (dose ratio=10:1; group e);

tofacitinib:crisaborole=2 mg:0.125 mg/20 μL (dose ratio=16:1; group f); tofacitinib:crisaborole=1 mg: 2 mg/20 μL (dose ratio=1:2; group g); tofacitinib:crisaborole=0.5 mg:2 mg/20 μL (dose ratio=1:4; group h); tofacitinib:crisaborole=0.25 mg:2 mg/20 μL (dose ratio=1:8; group i); tofacitinib:crisaborole=0.2 mg:2 mg/20 μL (dose ratio=1:10; group j); tofacitinib:crisaborole=0.125 mg:2 mg/20 μL (dose ratio=1:16; group k).
(2) Model Group
(3) Crisaborole (4 mg/20 ul)
(4) Tofacitinib (4 mg/20 ul)
(5) Blank group: applying with 20 μL DMSO as a solvent for comparison.
Experimental Method:

For the mice of each group, 20 ul (5 μg/20 μL/ear) of phorbol ester is applied to the front and back of the right ear for modeling, and 20 μL solvent medium (acetone) is applied to the left ear; except for the model group, the right ears of the mice in each administration group are applied with corresponding drugs 20 μL/ear 30 minutes before and 15 minutes after modeling, respectively. 6 h after modeling, the ear swelling is measured with a thickness gauge as an indicator of inflammation; then, the animals are sacrificed, the ears are cut and punched with a 6 mm punch, the ear pieces are weighed, and the swelling degree (weight) is calculated.
Experimental Results

TABLE 1

Effects of phorbol ester on the swelling degree of the auricle and inhibition rate of the swelling for the mice (ear thickness of $10^{-2}$ mm)

| Group | Dose (mg/20 μL) | Left ear (mm) (%) | Right ear (mm) | Swelling degree (mm) | Inhibition rate |
|---|---|---|---|---|---|
| blank |  | 30.1 ± 2.0 | 30.3 ± 2.3 | 0.2 ± 0.1 | — |
| model |  | 29.4 ± 1.8 | 48.4 ± 3.5 | 19.0 ± 4.4 | — |
| Tofacitinib | 4 | 29.3 ± 1.7 | 41.6 ± 3.4 | 12.4 ± 3.2$^{\triangle\triangle}$ | 34.7 |
| Crisaborole | 4 | 29.8 ± 1.7 | 43.0 ± 3.7 | 13.3 ± 3.4$^{\triangle}$ | 30.0 |
| a | 2/2 | 29.3 ± 1.6 | 36.9 ± 2.4 | 7.6 ± 1.3$^{\triangle\triangle**\#\#}$ | 60.0 |
| b | 2/1 | 28.9 ± 1.2 | 37.0 ± 2.5 | 8.1 ± 3.1$^{\triangle\triangle**\#\#}$ | 57.4 |
| c | 2/0.5 | 29.0 ± 1.1 | 37.4 ± 2.7 | 8.4 ± 3.3$^{\triangle\triangle*\#\#}$ | 55.8 |
| d | 2/0.25 | 29.1 ± 1.5 | 38.0 ± 3.1 | 8.9 ± 3.0$^{\triangle\triangle*\#}$ | 53.2 |
| e | 2/0.2 | 29.4 ± 1.2 | 39.4 ± 3.7 | 10.0 ± 3.0$^{\triangle\triangle}$ | 47.4 |
| f | 2/0.125 | 29.5 ± 1.4 | 41.3 ± 1.8 | 11.8 ± 2.1$^{\triangle\triangle}$ | 37.9 |
| g | 1/2 | 29.1 ± 1.5 | 37.6 ± 2.0 | 8.5 ± 2.4$^{\triangle\triangle*\#\#}$ | 55.3 |
| h | 0.5/2 | 29.1 ± 1.2 | 37.9 ± 3.0 | 8.8 ± 3.1$^{\triangle\triangle*\#}$ | 53.7 |
| i | 0.25/2 | 29.3 ± 1.7 | 38.4 ± 2.8 | 9.1 ± 2.0$^{\triangle\triangle*\#}$ | 52.1 |
| j | 0.2/2 | 29.4 ± 1.4 | 40.3 ± 3.1 | 10.9 ± 3.3$^{\triangle\triangle}$ | 42.6 |
| k | 0.125/2 | 29.3 ± 1.6 | 42.0 ± 3.2 | 12.8 ± 3.2$^{\triangle\triangle}$ | 32.6 |

Note:
$^{\triangle}$P < 0.05,
$^{\triangle\triangle}$P < 0.01 vs. model;
*P < 0.05,
**P < 0.01 vs. tofacitinib 4 mg/20 μL single use;
$^{\#}$P < 0.05,
$^{\#\#}$P < 0.01 vs. gram; crisaborole 4 mg/20 μL single use From above results, it can be known that a range of 16:1 to 1:16 for tofacitinib:crisaborole has a significant inhibition effect on the ear swelling of phorbol ester-induced mice, wherein when tofacitinib:crisaborole=1:8 to 8:1, the anti-inflammatory effect is better than when tofacitinib (4 mg/20 μL) and crisaborole (4 mg/20 μL) are used alone, thereby displaying significant anti-inflammatory synergy.

DESCRIPTION OF EMBODIMENTS

Embodiment 1

For ointment, the prescription is as follows:

| Component | Concentration (% W/W) |
|---|---|
| Crisaborole | 1.0% |
| Tofacitinib | 1.0% |
| Albolene | 60% |
| Glycerin monostearate | 10% |
| Propylene glycol | 19.98% |
| Glycerinum | 8% |
| Dibutyl hydroxytoluene | 0.02% |

A prescribed amount of crisaborole and Tofacitinib is taken, and dissolved or dispersed in a mixed solution of 27.98% propylene glycol and glycerin, then after they are evenly dispersed, an appropriate amount of antioxidant is added for mixing uniformly before use; another 70% white petrolatum and glycerin monostearate are taken in a stainless steel tank and heated, melted at 65° C.±5° C., then the temperature is remained, followed by slowly adding the above mixed solution into the melted matrix through mixing with a blender/homogenizer; after mixing for a period of time, the heat source is removed, and mixing is continued after cooling until completely homogeneous, so as to obtain the ointment.

The invention claimed is:
1. A pharmaceutical composition, comprising pharmaceutically active ingredients and a pharmaceutically acceptable carrier, wherein the pharmaceutically active ingredients are composed of tofacitinib and crisaborole in a range of 1:8 to 8:1 weight ratio of tofacitinib:crisaborole.

2. A method for treating skin inflammatory diseases, comprising applying the pharmaceutical composition according to claim 1 to a skin.

3. The method according to claim 2, wherein the skin inflammatory diseases are allergic dermatitis, urticaria, atopic dermatitis, seborrheic dermatitis, or contact dermatitis.

4. The method according to claim 2, wherein the skin inflammatory diseases are inflammatory skin reactions caused by psoriasis or systemic lupus erythematosus.

5. The pharmaceutical composition according to claim 1, having a dosage form of an external preparation.

6. The pharmaceutical composition according to claim 5, wherein the dosage form of the external preparation is cream, gel, foam, powder, tincture, lotion, spray or patch.

7. A method for treating skin inflammatory diseases, comprising applying the pharmaceutical composition according to claim 1 to a skin.

8. The method according to claim 7, wherein the skin inflammatory diseases are allergic dermatitis, urticaria, atopic dermatitis, seborrheic dermatitis, or contact dermatitis.

9. The method according to claim 7, wherein the skin inflammatory diseases are inflammatory skin reactions caused by psoriasis or systemic lupus erythematosus.

10. The pharmaceutical composition according to claim 1, having a dosage form of an external preparation.

11. The pharmaceutical composition according to claim 10, wherein the dosage form of the external preparation is cream, gel, foam, powder, tincture, lotion, spray or patch.

\* \* \* \* \*